US006187588B1

(12) United States Patent
Hui et al.

(10) Patent No.: US 6,187,588 B1
(45) Date of Patent: Feb. 13, 2001

(54) METHOD FOR INCREASING THE EFFICIENCY OF TRANSFECTION

(75) Inventors: Sek W. Hui, Williamsville; Shawn P. Murphy, Cheektowaga, both of NY (US); Lin H. Li, Fort Erie (CA); Arindam Sen, Wiliamsville, NY (US)

(73) Assignee: Health Research, Inc., Buffalo, NY (US)

( * ) Notice: Under 35 U.S.C. 154(b), the term of this patent shall be extended for 0 days.

(21) Appl. No.: 09/448,235

(22) Filed: Nov. 24, 1999

(51) Int. Cl.[7] .................................................. C12N 15/85
(52) U.S. Cl. ................................................. 435/455
(58) Field of Search ............................................. 435/455

(56) References Cited

U.S. PATENT DOCUMENTS 5,563,039 * 10/1996 Goeddel et al. ...................... 435/7.1

OTHER PUBLICATIONS

Uhlmann et al., J. Biol. Chem. 273: 17926–17932, A potent cell death activity associated with transient high level expression of BCL–2, Jul. 1998.*
Bird et al., Mol. Cell. Biol. 18: 6387–6398, Selective regulation of apoptosis: the cytotoxice lymphocyte serpin proteinase inhibitor 9 protects against granzyme B–mediated apoptosis without preturbing the Fas cell death pathway, Nov. 1998.*
Tatsuta et al., J. Immunology 157: 3949–3957, Intracellular IL–1beta is an inhibitor of Fas–mediated apoptosis, 1996.*

* cited by examiner

*Primary Examiner*—Robert A. Schwartzman
*Assistant Examiner*—Andrea Ousley
(74) *Attorney, Agent, or Firm*—Hodgson, Russ, Andrews, Woods & Goodyear LLP

(57) ABSTRACT

The present invention discloses a method for increasing the efficiency of transfection of cells by incubating the transfected cells with an inhibitor of apoptosis. In one embodiment, the inhibitor of apoptosis is a caspase inhibitor.

9 Claims, 12 Drawing Sheets

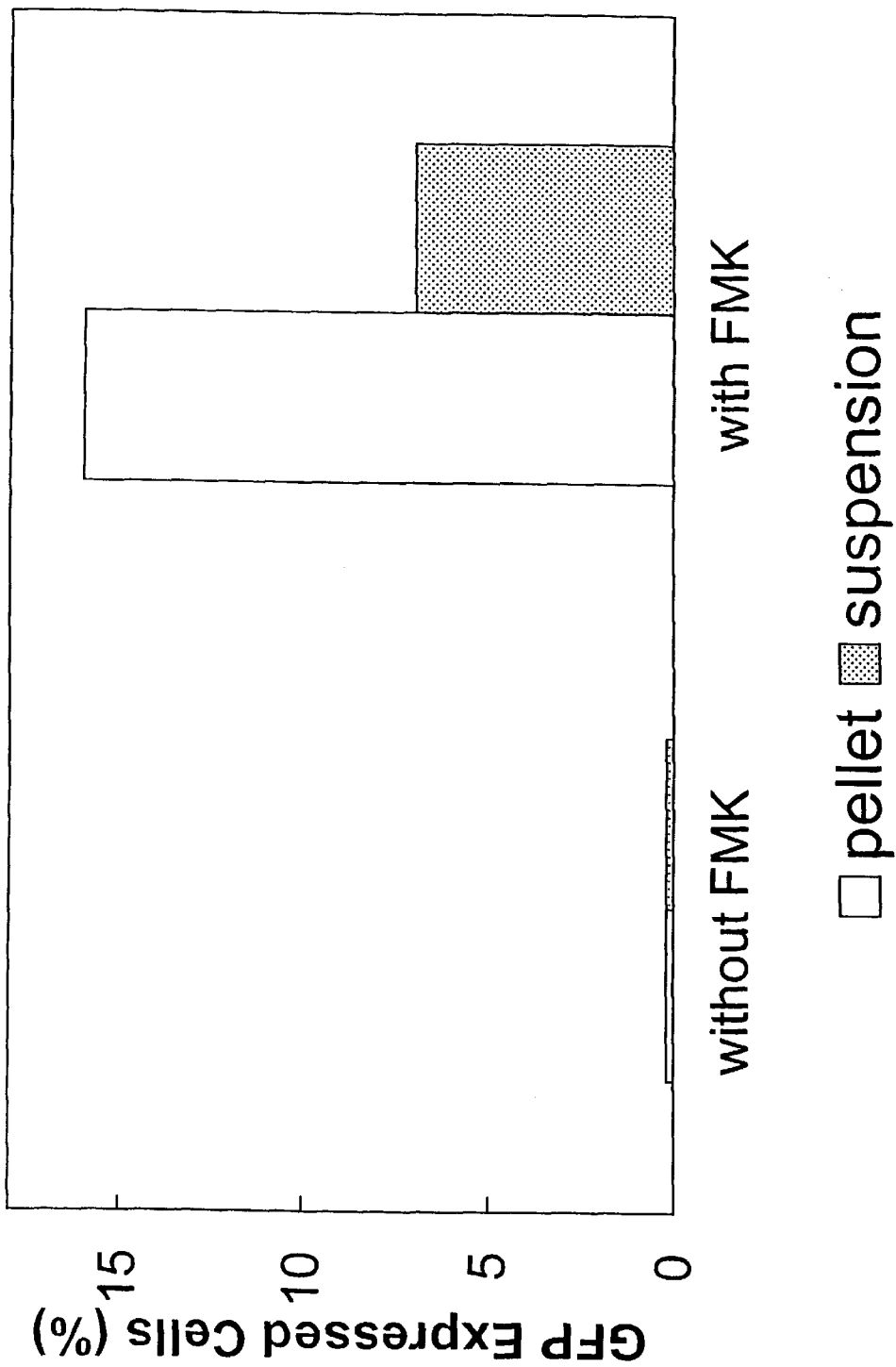

METHOD FOR INCREASING THE EFFICIENCY OF TRANSFECTION

This work was supported by grant number GM30969 from the National Institutes of Health. The government has certain rights in the invention.

BACKGROUND OF THE INVENTION

1. Field of the Invention

This invention relates generally to the field of genetic engineering, and particularly to the field of transfection of cells. More particularly, this invention provides a method for increasing the efficiency of transfection of cells by inhibiting cell death.

2. Description of Related Art

Transfection

Transfection of cells is routinely used as a genetic engineering tool. Transfection is the introduction of a foreign gene(s) into a target cell. Transfection methods can be useful in the areas of medicine, agriculture, pharmaceuticals, and Biomedical research. A particularly important application of transfection is gene therapy, wherein a foreign gene can be stably incorporated into a patient's genome thereby conferring upon the transfected cell, the ability to produce the product of the transfected gene.

The broad applicability of transfecting nucleic acid molecules into target cells, has led to the development of a number of protocols for performing transfections, many of which involve the use of carrier such as DEAE-dextran or calcium phosphate promoting the uptake of exogenous nucleic acids by cells. Other methods use cationic lipids for liposome induced uptake of nucleic acid sequences. Still other methods involve osmotic shock of cells or high-voltage electric pulses (electroporation) to create pores in cell membranes to facilitate uptake of nucleic acid molecules.

Electroporation is one of the common methods for transfection (Zimmermann, 1986, *Reviews of Physiology Biochemistry and Pharmacology.,* 105:176–256; Hui, 1995, *Methods in Molecular Biology,* 48:29–40). The high rate of transfection, simple control, and absence of biological contamination make electroporation a potentially promising method for gene therapy, especially in ex vivo cases (Bergan et al., 1996, *Blood* 88:731–741). However, the electrotransfection efficiency for certain cell types, particularly normal or malignant lymphocytes, is low. The reasons for the poor results are not known. Thus, identifying the reasons for the low transfection efficiency of lymphoid cells could have a significant impact on gene therapy and human health.

Apoptosis

Apoptosis, or programmed cell death, plays a critical role in the development and differentiation of multicellular organisms, cell homeostasis, immune function, and aging (Kerr et al., 1972, *Br. J. Cancer* 26:239–257; Sarin et al., 1996, *J. of Experimental Medicine* 184:2445–2450; Vaux et al., 1996, *Proc. Natl. Acad. Sci. USA* 93:2239–2244). Malfunctions of apoptosis are closely correlated with multiple forms of pathogenesis, including drug resistance and carcinogenesis (Vaux et al., 1998, *Nature* 335:440–442; Miyashita et al., 1993, *Blood* 81:151–159. Programmed cell death is an autonomous cellular process that is dependent upon the balance of relative levels of expression of members of the bcl-2 gene family (Oltvai et al., 1993, *Cell* 74:609–619; Chittenden et al., 1995, *Nature* 374:733–736). Apoptosis has been known to be responsible for death of traumatized cells. Previous studies demonstrated that transfection of cytokine-induced killer (CIK) T lymphocytes by receptor-mediated or cationic liposome-mediated transfection resulted in apoptosis (Ebert et al., 1997, 1997, *Gene Therapy,* 4:296–302). It was observed that these transfection methods induced the secretion of high levels of TNF-α by the transfected CIK T cells, which then activated the apoptotic pathway. Interestingly, only low levels of TNF-α secretion were detected from CIK T cells transfected by either electroporation or retroviral gene transfer.

With efforts continuing toward understanding the role of cell death in transfection, there is an ongoing need for improving the efficiency of transfection so as to achieve better results with gene therapy.

SUMMARY OF THE INVENTION

The present invention provides a method for improving the efficiency of transfection. The method is based on the unexpected finding that DNA-uptake induces apoptosis, and comprises the steps of exposing the transfected cells to inhibitors of apoptosis. The cells may be exposed to the apoptosis inhibitors during and/or after transfection.

BRIEF DESCRIPTION OF THE DRAWINGS

FIG. 8b is a graphic representation of transfection efficiency expressed as percent of fluorescent cells for post-pulse human hematopoietic cells, CD34+, incubated with or without the caspase inhibitor, fluoromethyl keone.

DETAILED DESCRIPTION OF THE INVENTION

Figure 1:
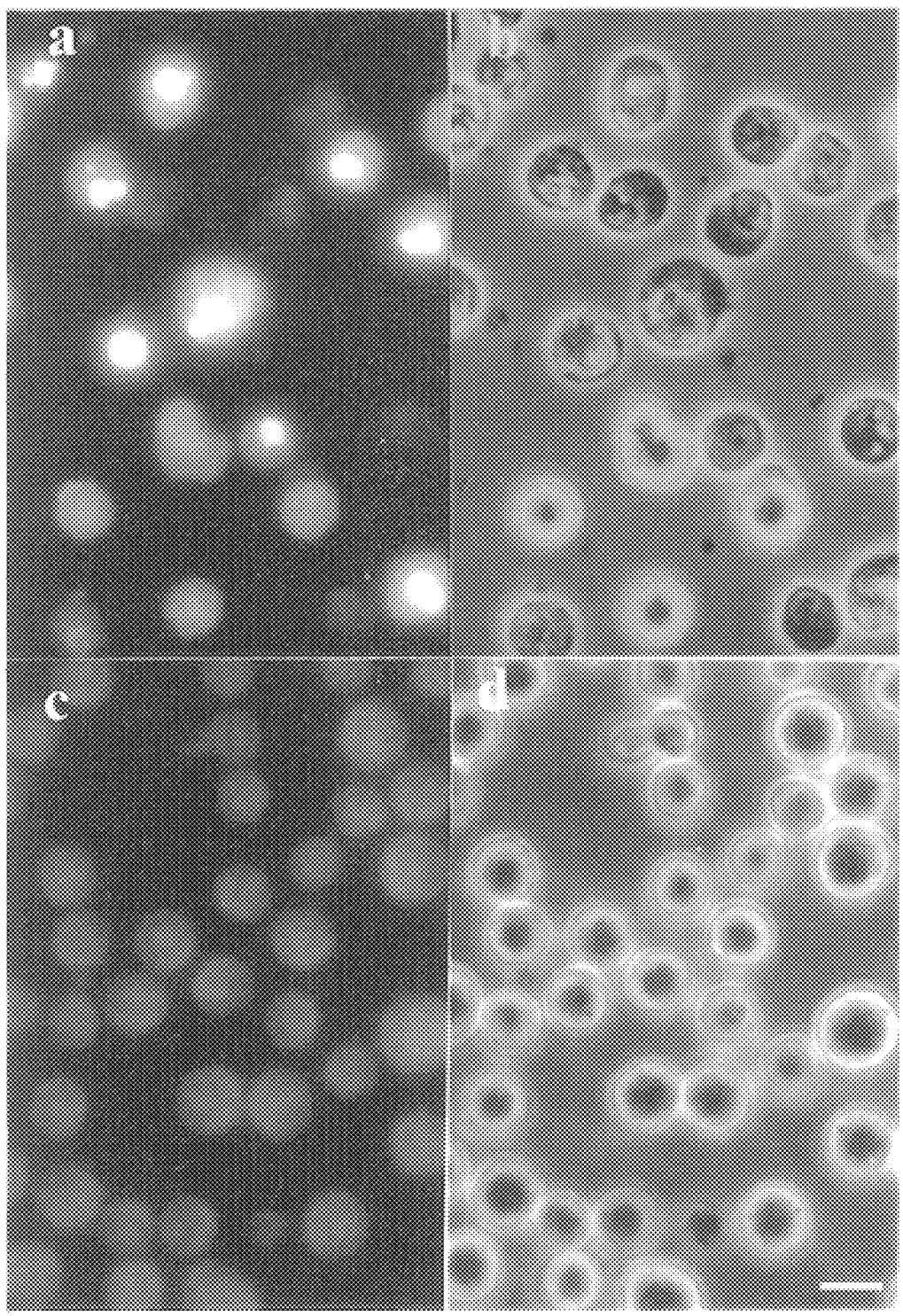
FIGS. 1a–d is a composite of fluorescence (a,c) and phase contrast (b,d) microscopic representations of the effect of electroporation on the morphology of L1210 subclone 3-3.

The present invention provides a method for increasing the efficiency of transfection.

As used herein, "transfection" means the introduction of nucleic acid sequences (including oligonucleotides), into a target cell.

As used herein, "transfection efficiency" or the "efficiency of transfection", refers to the degree of expression of the transfected gene in a given population of cells. The increase in transfection efficiency may occur by increased survival of transfected cells, increase in the percentage of cells being transfected, and/or increase in the amount of genes being transferred into, and/or expressed by cells.

The present invention has broad applications to all methods of transfection, well known to those skilled in the art. Various methods of transfection have been described in articles including, Kaufman—"Vectors Used for Expression in Mammalian Cells" in Methods in Enzymology, Gene Expression Technology edited by D. V. Goeddel, published by Academic Press, Inc., San Diego, 185-487–511, 1990; Keown et al., "Methods for Introducing DNA into Mammalian Cells" in Methods in Enzymology, supra, pp527–537; Kriegler et al., Gene Transfer and Expression, A laboratory Manual, published by W. H. Freeman & Co., New York, pp3–81, 1990; Davison et al., Molecular Virology, A practical Approach, IRL Press, Oxford University Press, Oxford, pp171–198, 1993. In addition, many kits for transfection are commercially available.

For the present invention, nucleic acids can be delivered to the target cell using any standard means known in the art. In general, two approaches have been used. The first approach is wherein the nucleic acids are introduced by biochemical or physical methods. Biochemical methods include, but are not limited to, pinocytotic uptake of DNA-calcium phosphate or DNA-dextran, and liposome mediated transfection methods. Physical transfection methods include direct injection of the nucleic acid sequence into a target cell using microcapillary or other microinjection devices, micro-projectile devices (such as Gene Gun from DuPont), and electroporation.

A second general approach for transfection is delivering nucleic acids into cells by infection. This approach uses a viral mediated process whereby target cells are infected with a virus whose genome carries the inserted cloned sequence of interest.

The DEAE-dextran based transfection was first described by Vaheri et al., (1965, *Virology*, 27:424–436), which disclosure is incorporated herein by reference. For this method, DEAE dextran, which is positively charged, is exposed to the DNA and binds to the negatively charged phosphate groups of the DNA, forming aggregates. Target cells are rinsed, and the DEAE-dextran/DNA mixture is added to the cells. After a suitable period of incubation, (such as 10–30 minutes) cells are washed and then incubated in a suitable growth medium. The optimal concentration of DEAE-dextran and the time of incubation varies with the cell type and can easily be determined by those skilled in the art.

The calcium phosphate transfection method was first described by Graham et al., (1973, *Virology*, 52:456–467), and modified by Wigler et al., (1979, *Proc. Natl. Acad. Sci. USA*, 76:1373–1376), Chen et al., (1987, *Mol. Cell Biol.*, 7:2745–2752), and Wurm et al., (U.S. Pat. No. 5,593,875), the disclosures of which are incorporated herein by reference. This method is based on the formation of insoluble calcium phosphate-DNA precipitates. The calcium ions bind to the negatively charged phosphate groups of the DNA. The phosphate ions help to precipitate the complex. While not intending to be bound by any particular theory, it is believed that the complexes attach to the surface of a target cell and are endocytosed. In general, the method comprises incubating the cells with calcium phosphate-DNA complex for a suitable time (such as 6–12 hours), and washing the cells, followed by incubation in a suitable growth medium.

The lipid-mediated transfection method, first described by Felger et al., (1987, *Proc. Natl. Acad. Sci. USA*, 84:7413–7416, which disclosure is herein incorporated by reference), is based on the formation of positively charged liposomes that attach to the negatively charged DNA and are attracted to the plasma membranes of target cells. For this method, cationic lipids can be used alone or in a mixture with neutral lipids. In general two types of lipids, monocationic and polycationic lipids (such as DOSPA) are used.

For transfection of cells by infection, viral carriers can be used. Such carriers include DNA viruses such as, but not limited to, SV40, polyoma, adenovirus, Epstein-Barr, vaccinia, herpes simplex papilloma particles, and baculovirus, and RNA viruses, including, but not limited to, tobacco mosaic virus, cucumber mosaic virus, brome mosaic virus, and retrovirus. The retrovirus may be a replication-incompetent virus such as replication incompetent retroviruses produced by packaging cell lines .psi.2, .psi.AM, PA12, PA317, PG13, clone 32 and the like.

For transfection using microinjection, a syringe needle, usually a heat-drawn sharp-ended glass tube, is used to puncture the target cell membrane to deliver a minute quantity of DNA solution. Often the needle is aimed at the nucleus, the ultimal destination of DNA, of the target cell for most efficient delivery. [Capecci, Cell 22:479–88, 1980; Mirzayans et al., Mutation Res. 281:115–22, 1992]. Aiming is actuated by using a micro-manipulator and viewed under a microscope. Once the target cells is punctured, a controlled quantity of DNA is injected by applying a controlled pressure to the syringe plunger. After microinjection, the target cells are left to recover. This procedure ensures that all target cells receive a known quantity of DNA. The drawback is that each cell has to be injected individually and manually. Thus the number of transfected cells is limited.

For transfection by projected particles, inert microscopic particles are coated or complexed with DNA, and propelled by a jet of high pressure gas to the target cells, using a pneumatic gun or the like (such as Gene Gun from Du Pont). The high speed particles perforate cell membranes and deliver the DNA load into cells. This method has been widely applied to deliver proteins, DNA and other molecules to cultured cells as well as cells on the surface of exposed tissues [Johnston et al., Genetic Eng., 15:225–236, 1993].

Electroporation is also a common method for introducing nucleic acid sequences into cells (see Hui, 1995, *Methods in Molecular Biology*, Chapter 2, 48:29–40). The method of electroporation consists of delivering high voltage pulses to target cells thereby making pores in the cell membrane to facilitate the transport of nucleic acid molecules into cells. The electroporation process consists of two major steps: reversible breakdown of the cell membranes, and recovery of permeablized cells. Certain level of membrane damage by pulse-induced membrane breakdown is needed for the nucleic acid molecules to enter cells. Equally important, the proper post-pulse incubation to recover the membrane impermeability is crucial for efficient transfection. Therefore, two sets of parameters (the electrical and incubation parameters) need to be balanced. Since both the electric breakdown of the cell membrane (electroporation) and the transfer of DNA across the plasma membrane by electrophoresis are physicochemical processes, the success of these steps should theoretically be independent of cell types.

The method of the present invention is carried out by transfecting cells by any of the standard techniques and then treating with an inhibitor of apoptosis. The inhibitor is added to the culture medium during post-pulse incubation. The inhibitor of apoptosis may also be present during electroporation. While the concentration of the apoptosis inhibitor may be dependent upon the particular choice of the inhibitor and the cell type, and can be easily determined by one skilled in the art, for L1210 cells, a range of 1 $\mu$M to 1 mM has been found to be useful. Many inhibitors of apoptosis are known in the art and include, but are not limited to, caspase inhibitors and calpain inhibitors. The caspase inhibitors include, but are not limited to, fluoromethyl ketone (FMK), and its various derivatives. Many of these derivatives are commercially available (Enzyme Systems Products), and include, Z-VAD-FMK, Z-DEVD-FMK, Boc-Asp-FMK, Z-IETD-FMK, Z-YVED-FMK, Z-VEID, Z-VDVAD, Biotinlyated-VAD-FMK. Further, other known inhibitos of Apoptosis are described in U.S. Pat. No. 5,972,899 and include products of genes such as bcl2 gene from certain human tumors, bhrf1 gene of the Epstein-Barr virus, lmw5-hl gene of African swine fever virus, p35 gene and the iap gene in baculoviruses.

The invention will be understood better from the examples presented below, which are to be construed as illustrative and not restrictive. In most of the examples below, electroporation has been used as a means for transfecting cells. However, those skilled in the art will appreciate that the embodiments are applicable to all transfection methods.

EXAMPLE 1

This example illustrates the cell preparation and electroporation protocols used for the subsequent examples.

L1210 parental cells, and subclones 3-3, 4, 6 and 7-15.6 (Fuji et al., 1986, *Cancer Research*, 46:5541–5547.), erythroleukemia K-562 and MC-2 (mouse mammary tumor cells) were cultured in RPMI-1640 with 10% FBS. These cells are accepted as a model for the study of tumorigenicity as well as the efficacy of chemotherapeutic agents (Mihich et al., 1969, *Cancer Reasearch* 29:848–854; Fuji et al., 1975, *Cancer Research* 35:946–952; Fuji et al., 1986, supra). NK-L cells were cultured in the same medium plus 20 ng/ml interleukin-2. NFS-70 pro-B cells (Davidson et al., 1984, *J. Immunol.*, 133:744–753) were cultured in DMEM with 10% FBS. CHO cells were cultured in F10 medium with 15% newborn calf serum. 0.6% (in volume) of penicillin (50 $\mu$g/ml)-streptomycin (50 $\mu$g/ml)-neomycin (100 $\mu$g/ml) antibiotic mixture was used in cell culture. CD34+ cells were isolated from human donor blood, and the mouse bone marrow dendritical cells, BM-DC, were isolated according to the method of Lutz et al., (1999, *J. Immunol. Methods*, 223:77–92). Prior to transfection experiments, cells were centrifuged, resuspended into B&K medium (125 mM KCl, 15 mM NaCl, 25 mM Hepes, 3 mM glucose, pH 7.4) or respective cell culture medium at a concentration of 2–10× $10^7$/ml, and kept at room temperature before use. All chemicals for cell culture were obtained from Life Technology (Grand Island, N.Y.).

Five volumes of suspended cells were mixed with one volume of plasmid at different concentrations in STE buffer (100 mM NaCl, 10 mM Tris-HCl, 1 mM EDTA, pH8). The plasmids, pGL3-control (Promega, Madison, Wis.) and pEGFP-N1 (CLONTECH Lab. Inc., Polo Alto, Calif.) coding for luciferase and green fluorescence protein, respectively, were isolated by using the QIAGEN plasmid Mega kits from Qiagen Inc. (Santa Clarita, Calif.). Cells (15 $\mu$l, $8\times10^5$ $15\times10^5$ cells) were placed in a customer-built stainless electrode chamber, and a quasi-square pulse with 400 s width and 1.7 kV/cm field strength (unless mentioned specifically) was applied. After pulsing, cells were immediately suspended into 100 $\mu$l culture medium in an eppendorf tube, incubated in suspension at 37C. in a small water bath inside a cell-culture incubator for 20 min, and subsequently resuspended into culture medium for growth.

EXAMPLE 2

This embodiment illustrates that electroporation induces apoptosis. During transfection studies in L1210 lymphoma cells, it was observed that certain subclones were apparently extremely refractory to transfection by a variety of methods including calcium phosphate and cationic liposomes. When electroporation was used at pulse conditions that were milder than those used for other cell lines, such as CHO and erythroleukemia K-562 cells, it was observed that the vast majority of cells survived immediately after electroporation, but died after several hours of incubation. While not intending to be bound by any particular theory, it is believed that the relatively slow onset of cell death is because apoptosis was involved.

To further illustrate this embodiment, L1210 subclone 3-3 cells were evaluated for apoptosis following transfection with plasmid pGL3-control (Promega) as disclosed in Example 1. The pGL3-control plasmid contains the firefly luciferase gene under the control of the SV40 promoter/enhancer, as disclosed in Example 1. Apoptotic cells were distinguished from living cells by staining with the fluorescent dye propidium iodide/acridine orange, which shows the condensation of chromatin and the fragmentation of nuclei within 24 hours after electroporation. Apoptotic cells were also distinguished by a characteristic morphology that is the result of changed refractivity due to apoptosis, the nuclear fragmentation and nucleosomes, observable by phase contrast and fluorescence microscopy, according to the method of Williams et al., (1994, *J. Immunology* 153:4247–4255). Fluorescence and phase contrast micrographs of the same fields of view are shown in FIG. 1. Cells in (a, b) were pulsed with 400 $\mu$g/ml luciferase plasmid DNA, whereas those in (c, d) were pulsed without plasmid DNA. Cells were stained by propidium iodide/acridine orange (100 $\mu$g/ml and 10 $\mu$g/ml, respectively) in (a) and (c). One 400 $\mu$s, 1.7 kV/cm pulse was applied. The bar is 12 $\mu$m. As shown in FIG. 1*a*, propidium iodide/acridine orange staining of L1210 subclone 3-3 pulsed in the presence of 400 ug/ml luciferase plasmids revealed chromatin clumping and nuclear fragmentation that is characteristic of apoptosis within 24 hours after electrotransfection. This apoptotic morphology was also clearly observed by phase contrast microscopy (FIG. 1*b*). However, when the cells were pulsed in the absence of DNA, they maintained their shiny intact cell shape (FIG. 1*d*), a pale green fluorescence color, and a viability comparable to non-transfected cells (FIG. 1*c*). Replacing potassium rich B&K medium with sodium rich culture medium as pulsing medium (RPMI-1640 for L1210 subclones or DMEM for NFS-70 Pro-B cells), with or without 10% FBS, or Ca$^{++}$, had no effect on the percentage of apoptotic cells, determined by counting under phase contrast microscopy.

In another illustration of this embodiment, the relationship between cell death and the ease of electrotransfection of cells was determined. Three additional cell lines (L1210 subclones 4, 6 and NFS-70 pro-B cells) that are also highly refractory to various transfection methods, and several more cell lines that are not refractory to electrotransfection (parental L1210, subclone 7-15.6, CHO, NK-L, MC-2, and erythroleukemia K-562) were studied. It was found that the cell lines that are refractory to transfection methods (L1210 subclones 4 and 6 and NFS-70 pro-B cells) undergo apoptosis. As shown in Table 1, the level of apoptosis for the three L1210 subclones (3-3, 4, 6) is comparable when cells were pulsed in the presence of 600 μg/ml plasmids coding for luciferase (about 50%). The level of apoptosis for NFS-70 pro-B cells is about 12%. None of the other cell lines, including parental L1210 and subclone 7-15.6 cells, showed significant electrotransfection-induced apoptosis. These data suggest that the refractoriness to transfection may be due to apoptosis.

In yet another illustration of this embodiment, some features of the cell death associated with electrotransfection in L1210 clones was studied. One of the characteristics of apoptosis is the ordered cleavage of DNA into discrete sized fragments that can be detected by gel electrophoresis (Wyllie, 1980, *Nature* 284:555–556; Arends et al., 1990, *Am. J. Pathol.* 136:593). To further verify that the transfected cells do undergo apoptosis, genomic DNA of L1210 subclone 3-3 was isolated following electroporation and analyzed by gel electrophoresis by the following method.

Cells ($5 \times 10^6$) were washed once in PBS (150 mM NaCl, 3 mM KCl, 5 mM NaPi, pH7.4) and resuspended in 400 μl of DNA isolation buffer (0.15 M NaCl, 0.015 M Na Citrate, 0.01 M EDTA, and 1% Lauryl Sarkosinate) with added Proteinase K (0.5 mg/ml), and incubated at 50° C. for two hours. DNA was precipitated with two volumes of cold ethanol, placed at –80° C. for 20 min, and centrifuged at 13,000 g at 4° C. for 10 min. The vacuum dried DNA was resuspended in 400 μl of TE buffer (10 mM Tris, 1 mM EDTA, pH8.0), digested with RNase A (0.5 mg/ml) for 2 hours at 37° C., and stored at –20° C. DNA ladders (5 μg/sample) were resolved on 1% agarose/1×TBE gels (90 mM Tris, 90 mM Boric acid, 2 mM EDTA, pH8.0) containing ethidium bromide and visualized using ultraviolet light.

Figure 2:
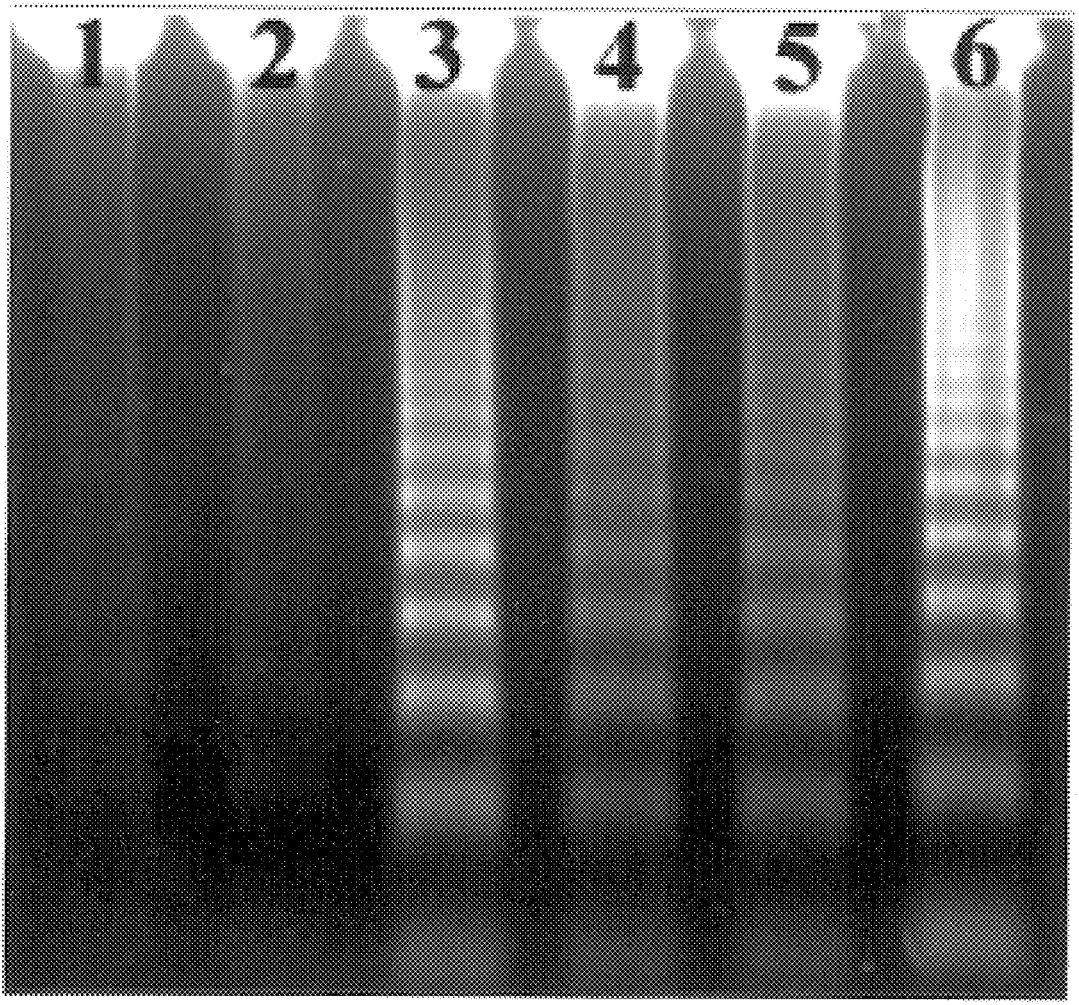
FIG. 2 is a photographic representation of gel electrohporesis of genomic DNA of L1219 subclone 3-3 incubated with luciferase plasmid DNA for pulsed and non-pulsed cells.

The results are shown in FIG. 2. Lanes 1–5 in FIG. 2, represent the DNA isolated 24 hours after electroporation, and lane 6 represents the DNA isolated 6 hours after electroporation. DNA isolated from cells pulsed in the presence of various concentrations of plasmid DNA (lanes 3–5, 100 μg/ml, 200 μg/ml, and 400 μg/ml, respectively) showed the DNA laddering structure characteristic of apoptosis. Laddering structure of DNA isolated 6 hours after pulsing demonstrated that apoptosis occurs within 6 hours after pulsing (lane 6). In contrast, DNA laddering was not observed with genomic DNA isolated from cells pulsed in the absence of plasmid DNA (lane 1) or incubated with plasmid DNA (400 μg/ml) but not pulsed (lane 2). Thus, electroporation of L1210 subclone 3-3 in the presence of plasmid DNA appears to induce apoptosis.

Figure 3A:
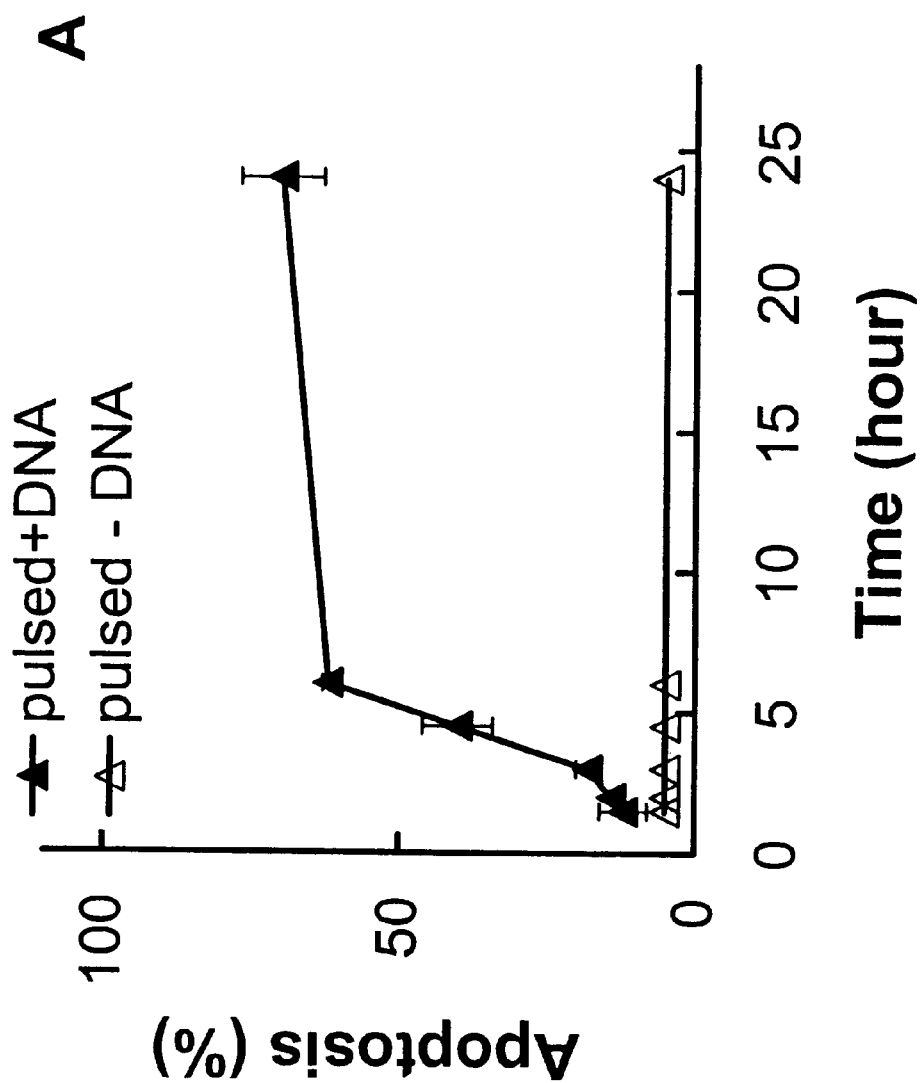
FIG. 3A is a graphic representation of the time dependence of apoptosis of L1210 subclone 3-3 after pulsing with (solid triangles) or without (empty triangles) 800 µg/ml luciferase plasmid DNA.
Figure 3B:
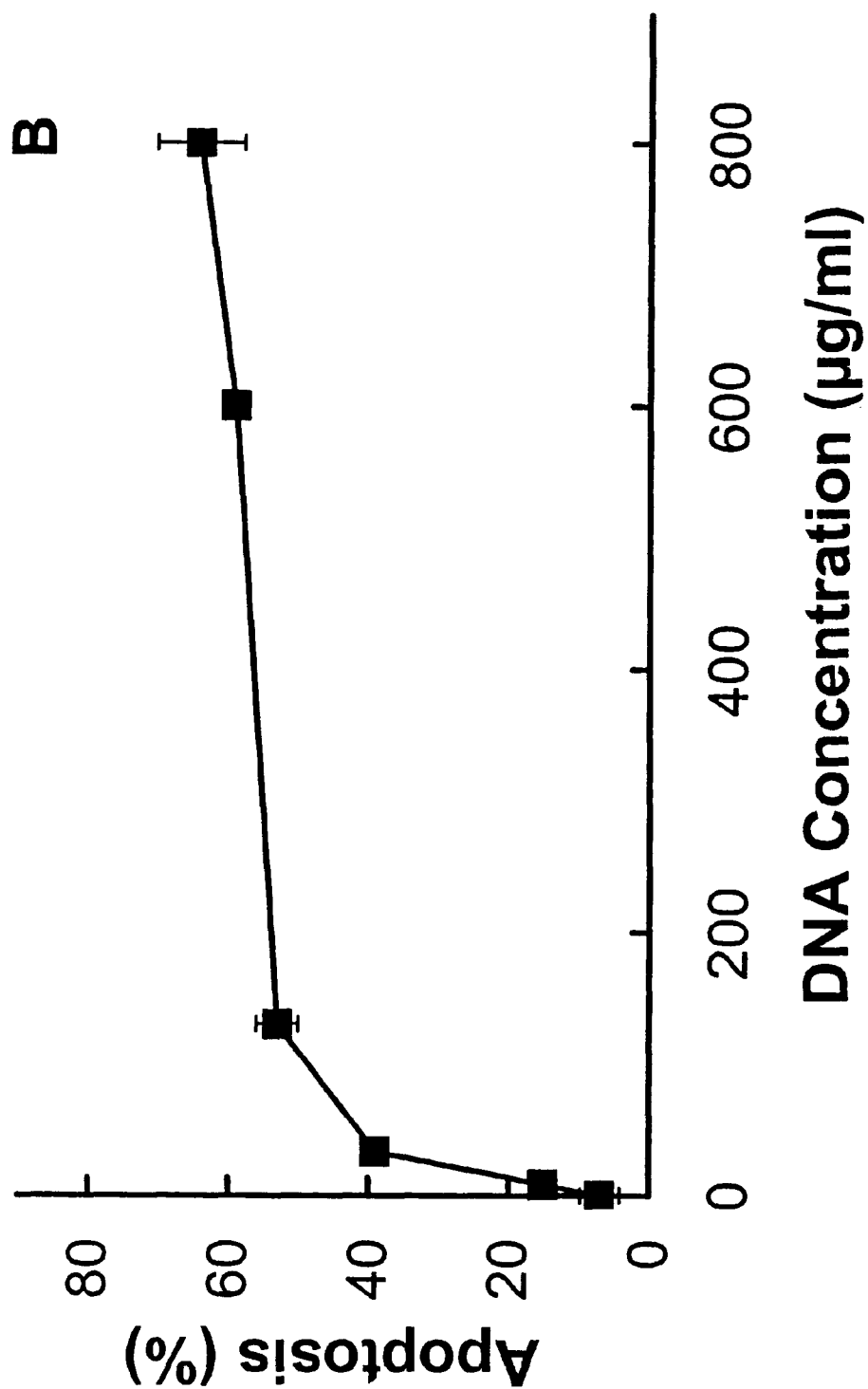
FIG. 3B is a graphic representation of the effect of luciferase plasmid DNA concentration on apoptosis of L1210 subclone 3-3.

In yet another illustration of this embodiment, the kinetics of apoptosis of L1210 subclone 3-3 was studied by examining the morphology of the cells at various times after transfection (FIG. 3A). The curve with solid triangles represents the apoptosis of cells in the presence of 800 ug/ml luciferase plasmid DNA. The curve with empty triangles represents the apoptosis of cells pulsed in the absence of plasmid DNA. Cells were pulsed by one 400 μs, 1.7 kV/cm pulse. When cells were pulsed in the presence of plasmids coding for luciferase, apoptosis was observed within 4 hours after pulsing, increasing very quickly at 4–6 hours, and reaching greater than 70% of the total cell population within 24 hours. When cells were pulsed in the absence of plasmid DNA, no significant apoptosis was observed. The effect of luciferase plasmid DNA concentration on apoptosis of L1210 subclone 3-3 cells was also studied by pulsing with one 400 μs, 1.7 kV/cm pulse. As shown in FIG. 3B, the apoptosis is plasmid DNA concentration-dependent, increasing dramatically in the low DNA concentration region (<150 μg/ml), and leveling off at DNA concentrations at or above 150 μg/ml.

EXAMPLE 4

This embodiment demonstrates that transfection efficiency is limited by apoptosis. To illustrate this embodiment, L1210 subclone 3-3 cells were electrotransfected as described in Example 1. Luciferase activity was measured using a commercial kit (Promega luciferase assay kit). Briefly, cells were harvested and centrifuged at the given time after pulsing, lysed in 100 μl of lysis buffer, and subjected to one round of freeze-thawing. The luminescence of 20 μl of lysate was measured using a luminometer (Lumat model LB9501, Berthold, Germany) and standardized by using known concentrations of luciferase. The expression of green fluorescence protein was assayed by observing the fluorescence of cells under phase and fluorescence microscope. The percentage of the fluorescent cells was used as an indicator of transfection efficiency.

Figure 4:
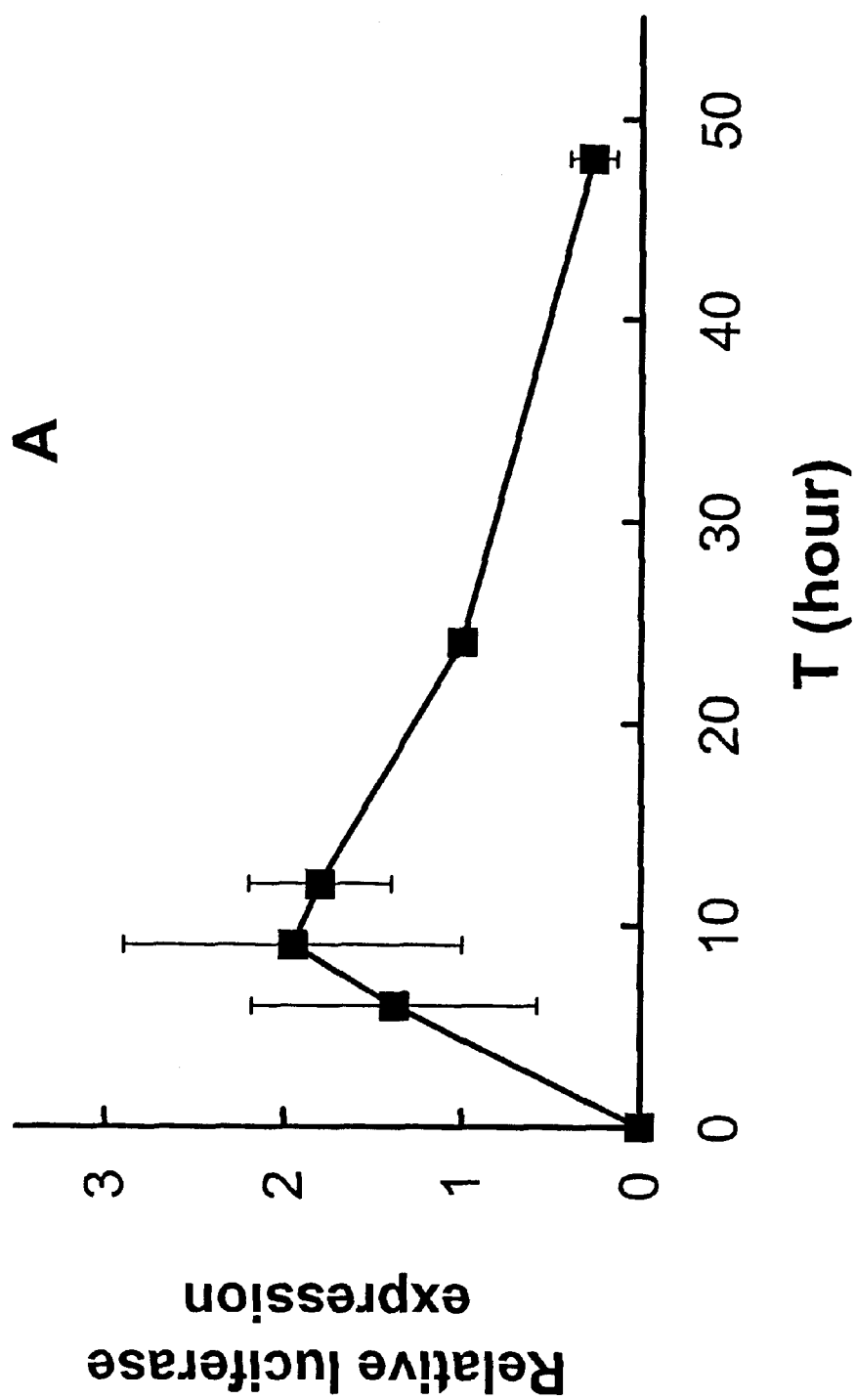
FIG. 4 is a graphic representation of the time dependence of relative luciferase expression of L1210 subclone 3-3.

The luciferase expression was normalized against that at 24 hours after pulsing. One 400 μs, 1.7 kV/cm pulse was applied with the presence of 600 μg/ml luciferase plasmids. FIG. 4 shows the kinetics of luciferase expression. The initial increase (assayed within 6–12 hours after pulsing) and subsequent decrease (>12 hours) of luciferase expression of L1210 subclone 3-3 after pulsing suggests that the transfection efficiency may be limited by apoptosis. The luciferase expression assayed at 24 hours after pulsing dropped to about half that at 12 hours. At 48 hours after pulsing, the luciferase expression dropped by another ten-fold.

Figure 5:
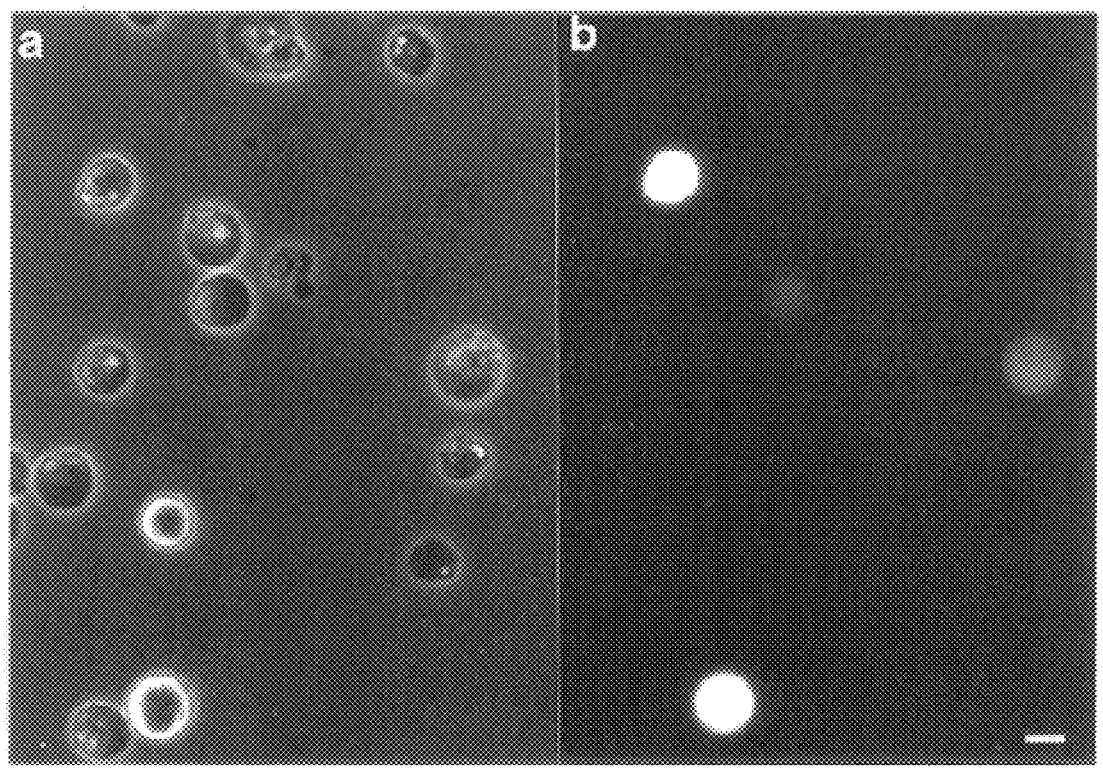
FIGS. 5a–b is a composite of phase contrast (a) and fluorescence (b) microscopic representations of the time dependence of relative luciferase expression in L1210 subclone 3-3.

If apoptotic cells can express transgene, then the drop in transgene expression at >12 hours can be attributed, at least partially, to apoptosis of transfected cells. In order to test this, L1210 subclone 3-3 was electroporated with plasmid pEGFP-N1 (Clontech), by one 400 μs, 1.7 kV/cm pulse. This plasmid contains the gene encoding the jellyfish green fluorescence protein (GFP) under the control of the SV40 promoter/enchanter. The morphology of these cells was studied by phase contrast and fluorescence microscopy. A pair of phase (FIG. 5a) and fluorescence (FIG. 5b) micrographs of L1210 subclone 3-3 were taken at 12 hours after electroporation (300 μg/ml pEGFP-N1 plasmid). As shown in FIG. 5b, certain apoptotic cells express green fluorescent protein. The fact that a substantial portion of apoptotic cells express transgene suggests that the above postulation is reasonable. Since certain non-apoptotic cells also express GFP, it indicates that DNA-uptake does not necessarily lead to apoptosis.

EXAMPLE 5

Figure 6:
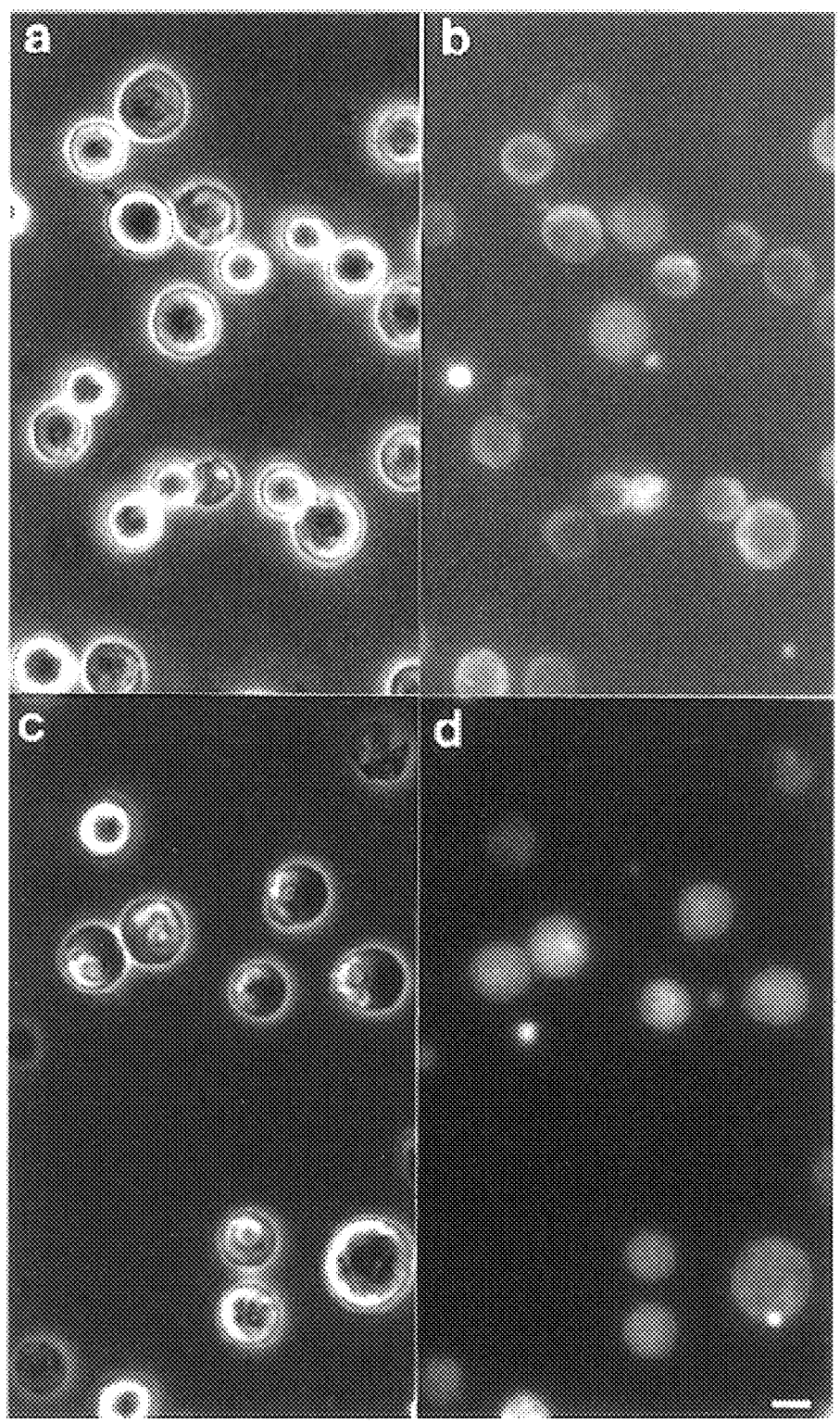
FIGS. 6a–d is a photographic representation of the phase contrast (a,c) and fluorescence (b,d) views of uptake of luciferase plasmid DNA at 20 min (a, b) or 5 hours (c, d) after electroporation.

This embodiment demonstrates that apoptosis is induced by the uptake of DNA by cells. To illustrate this embodiment, it was first determined if all apoptotic cells contain DNA. Dialyzed complexes of luciferase plasmids DNA (25 bp/YOYO) and YOYO™ (a dimeric cyanin nucleic acid stain from Molecular Probes, Eugene, OR) were used to trace DNA after electroporation, since DNA/YOYO complex will not dissociate when ratio of base-pair/YOYO is higher than 10 (Rye et al., 1992, *Nucleic Acids Research,* 20(11):2803–2812. Dialyzed YOYO-DNA complexes (25 base-pair/YOYO) at 400 μg/ml luciferase plasmid DNA concentration were used for electroporation (one 1.7 kV/cm, 400 μs pulse). The uptake of luciferase plasmid DNA is shown in FIGS. 6a–d. The bar is 10 μm. As shown in FIGS. 6a, b, and c, d, two pairs of phase contrast and fluorescence micrographs of cells 20 min and 5 hours after electroporation respectively, all cells showed YOYO fluorescence. The fluorescence intensity of cells increased when the concentration of DNA/YOYO complexes in the pulsing medium increased (data not shown). Furthermore, as shown in FIGS. 6c, d, all apoptotic cells contained YOYO-DNA complexes. This demonstrated that DNA entered the cytoplasm of all electroporated L1210 subclone 3-3 cells, including all apoptotic and non-apoptotic cells. Since cells that were electroporated in the absence of DNA do not undergo apoptosis (FIGS. 1c, d), the above data show that apoptosis is induced not by the presence but by the uptake of plasmid DNA.

In another illustration of this embodiment, L1210 subclone 3-3 was electroporated in the presence of either 1) plasmid pGL3-basic (Promega), which contains the luciferase coding region, but lacks a functional promoter sequence, or 2) salmon sperm DNA. In both instances, a significant percentage of cells was observed to undergo apoptosis (Table 2). These results suggest that the induction of apoptosis of L1210 subclones is due to uptake of exogenous DNA, and not expression of transgenes. Furthermore, the fact that both supercoiled plasmid DNA and linear salmon sperm DNA induces apoptosis indicated that cell death is independent of the conformation of the introduced exogenous DNA.

EXAMPLE 6

This embodiment demonstrates that phenomenon of apoptosis as described herein, is independent of the transfection method. To illustrate this embodiment, cationic lipid DOTAP was used as follows to transfer DNA into L1210 subclone 3-3.

DOTAP (1,2-Dioleoy-3-Trimethylammonium propane, Avanti Polar Lipids, Alabaster, Ala.) vesicles were made by drying the DOTAP lipid under nitrogen gas and resuspending in distilled water by vortexing. DNA-DOTAP complex was formed by mixing 25 ug of DNA (2.6 mg/ml) and 25 ul of DOTAP (1.4 or 2.8 mg/ml), which gave a charge ratio of 1:2 or 1:1 (lipid to DNA). The DNA-DOTAP complex (8 ul or 16 ul) was added to 100 ul of cell suspension in 96 well culture plates immediately after complex formation, to reach a final DNA concentration of 60 or 120 ug/ml, respectively. The DNA-DOTAP complex remained in the cell suspension during cell culture. No toxic effect of DNA-DOTAP complex on cell viability was observed. The transfection efficiency was assayed 24 hour later. Plasmids coding for green fluorescence protein were used for detecting protein expression and apoptosis of individual cells simultaneously. As shown in Table 3, though the apoptosis and transfection efficiency are both low (<5%), the percentage of apoptotic cells among the population of cells expressing green fluorescence protein is disproportionally high (75% and 95% for DNA:DOTAP charge ratio 1:1), and 52% and 47% for DNA:DOTAP charge ratio 1:2) at 60 μg/ml and 120 μg/ml of DNA concentrations, respectively. This further supports that uptake of DNA induces apoptosis, and that the phenomenon of apoptosis is independent of the method of transfection.

EXAMPLE 7

This embodiment demonstrates that using an inhibitor of apoptosis increases transfection efficiency. To illustrate this embodiment, post-pulse cells were incubated with a caspase inhibitor. Boc-Asp-FMK is a general caspase inhibitor that has been shown to suppress apoptosis of lymphocytes induced by many stimuli (Sarin et al., 1996, *J. of Experimental Medicine* 184:2445–2450; Henkart et al., 1997, *Immunology* 9:135–144). The effect of caspase inhibitor (Boc-Asp-FMK) on apoptosis induced by DNA uptake and luciferase expression of L1210 subclones 3-3, 4 and 6 and NFS-70 pro-B cells was examined. Cells were pulsed by one 400 μs, 1.7 kV/cm pulse in the presence of 600 μg/ml luciferase plasmids.

Figure 7A:
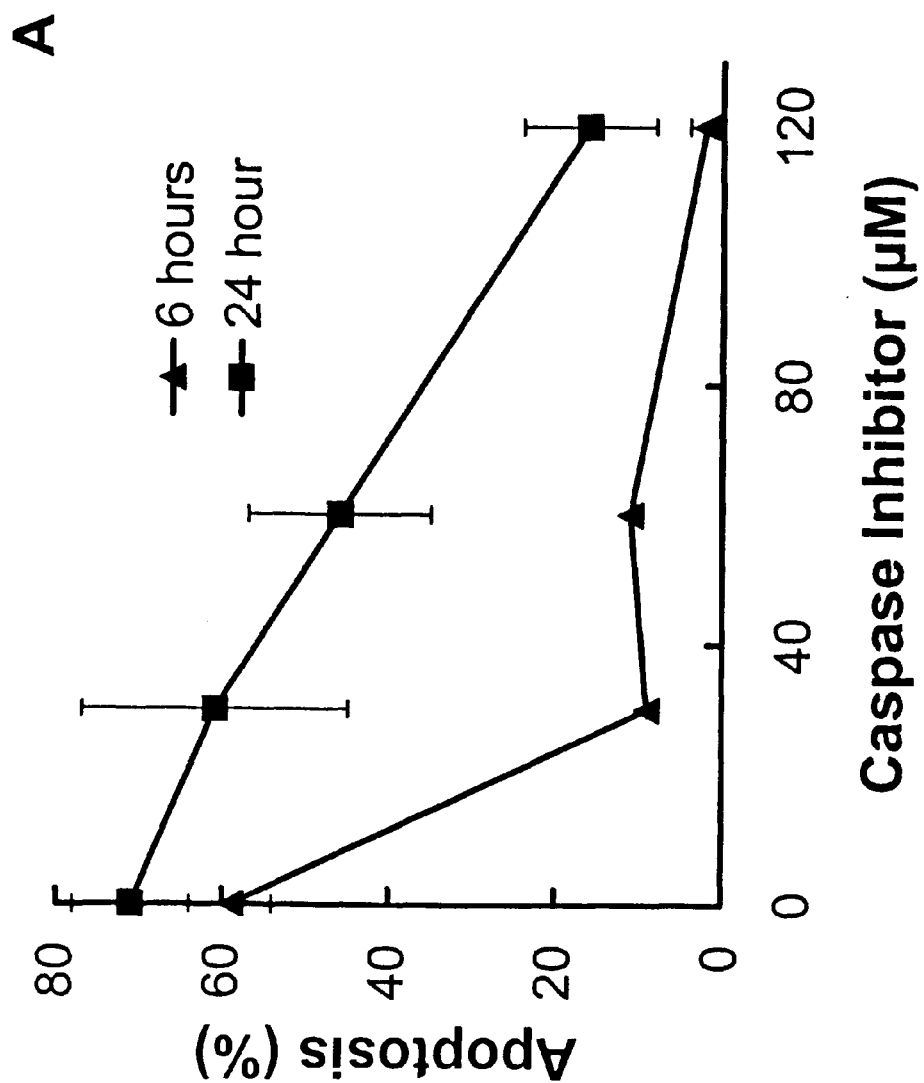
FIG. 7A is a graphic representation of the effect of a caspase inhibitor on apoptosis in L1210 subclone 3-3.

The results are shown in FIG. 7. The curves with triangles and squares represent the apoptosis of cells assayed 6 and 24 hours after pulsing, respectively. As shown in FIG. 7A, Boc-Asp-FMK reduces apoptosis of L1210 subclone 3-3 induced by the DNA uptake in a concentration-dependent manner. At 120 μM, the most effective concentration found, Boc-Asp-FMK reduced the apoptosis of L1210 subclone 3-3 from 72% (24 hour assay) or 59% (6 hour assay) to 20%–10% respectively. Similar decreases in the rate of apoptosis of L1210 subclone 4 and 6 and NFS-70 pro-B cells were observed when 120 μM of Boc-Asp-FMK were used (table 1).

Figure 7B:
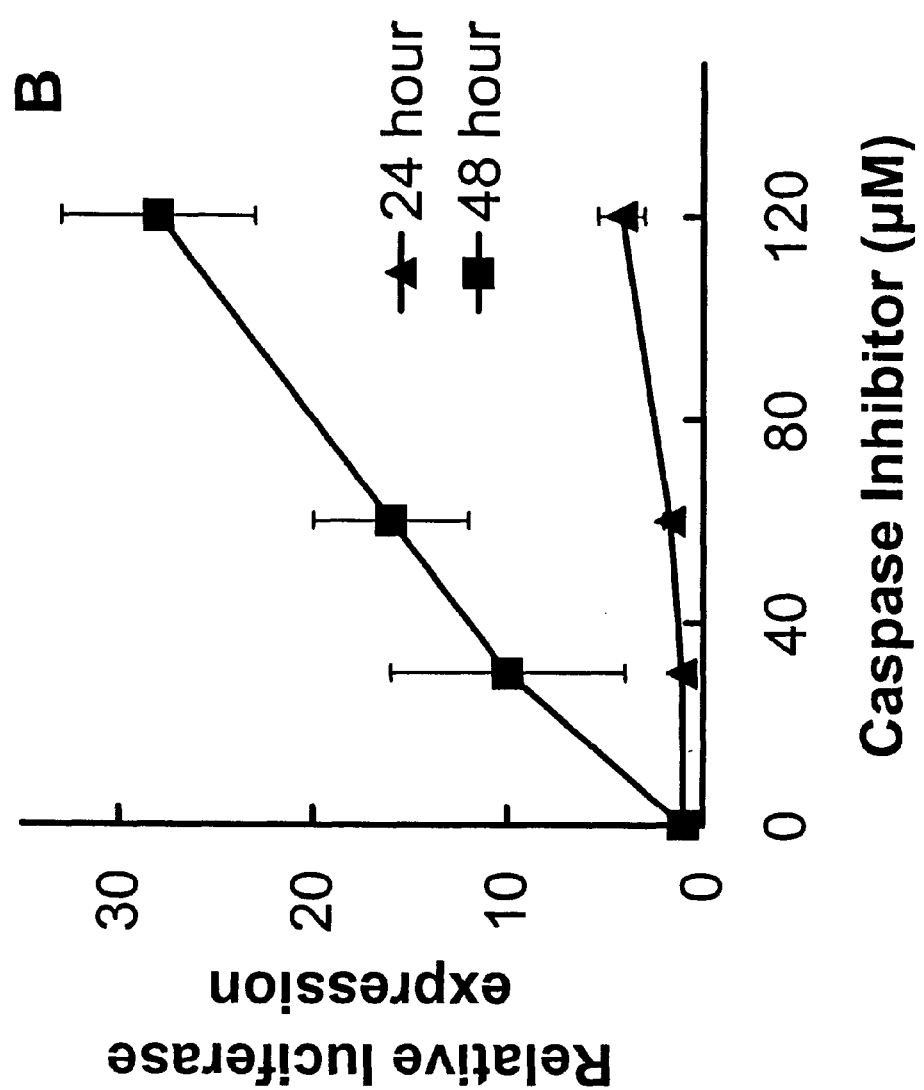
FIG. 7B is a graphic representation of the effect of a caspase inhibitor on transfection efficiency measured as relative luciferase expression in L1210 subclone 3-3.

Further, the effect of caspase inhibitors on the relative luciferase expression of L1210 subclone 3-3 was studied and is shown in FIG. 7B. The luciferase expression at 24 or 48 hours was normalized against that without inhibitor at 24 or 48 hours respectively. The curves with triangle and square represent luciferase expressions assayed 24 and 48 hours after pulsing respectively.

Since the luciferase expression varies for different experiments, but the trend of the effect of caspase inhibitor on luciferase expression was always the same, the luciferase expression at 24 or 48 hours was normalized against that at 24 or 48 hours without inhibitor, respectively. A strong concentration-dependent manner of inhibitor is also observed on luciferase expression. Inclusion of 120 μM of the caspase inhibitor resulted in the highest improvement, about 4 fold of increase in luciferase activity at 24 hours, and 28 fold of increase of luciferase activity at 48 hours. The same effect of caspase inhibitor (120 μM) on increase of transgene expression was observed on L1210 subclones 4 and 6 and NFS-70 pro-B cells (Table 1). 4.6 (subclone 4), 8 (subclone 6), and 4.6 (NFS-70 pro-B cells) fold of increase of luciferase activity were observed when assayed at 24 hours after pulsing respectively, and 37 fold of increase for NFS-70 pro-B cells when assayed at 48 hours after pulsing. These results demonstrate that apoptosis plays a significant role in reducing the transfection efficiency of select L1210 subclones and NFS-70 pro-B cells.

The transfection efficiency of parental L1210 cells was compared to that of L1210 subclone 3-3 cells when caspase inhibitor (120 μM) was used. The transfection efficiency (ng luciferase/million pulsed cells assayed at 24 hour post pulse)

of 2.7±2.6 for 3-3 subclone cells is comparable within experiment error with the value of 3.9+1.6 for parental L1210 cells. This indicates the low transfection efficiency of the former can be rescued by inhibition of apoptosis.

EXAMPLE 8

Figure 8A:
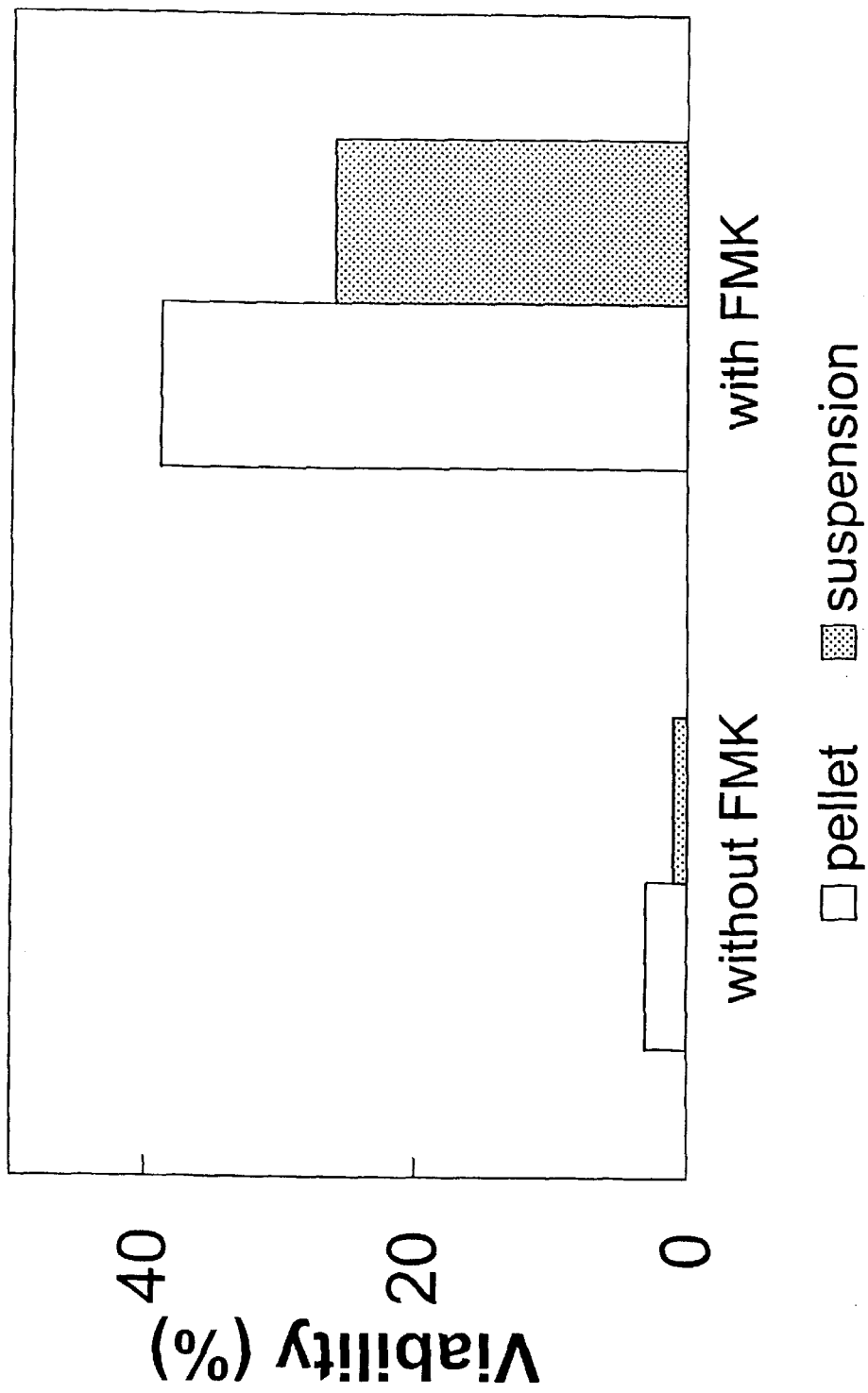
FIG. 8a is a graphic representation of post-pulse viability for the human hematopoietic cells, CD34+, incubated with or without the caspase inhibitor fluoromethyl ketone.

This embodiment demonstrates that the effect of apoptosis inhibitor on transfection efficiency is not limited to L1210 cells, but is a generalized phenomenon. To further illustrate this embodiment, human peripheral blood CD34+ cells were used. These cells are known to be difficult to transfect, with the transfection efficiency by retroviruses reported to be only 1–2%. In this illustration, CD34+ cells were isolated from human donor blood, using a Miltanyi magnetic bead immuno-separation device, or by FACS. After electroporation, cells were pelleted or allowed to remain suspended for 20 minutes before being transferred to culture medium (Stem-Pro, GIBCO, Grand Island, N.Y.). Transfection efficiency was evaluated. Without caspase inhibitor most cells underwent apoptosis after electroporation, with or without post-pulse pelleting. Adding the caspase inhibitor, fluoromethyl ketone, rescued about 40% of CD34+ cells after pulse application, especially cells that are were post-pulse pelleted (FIG. 8a). Using plasmids coding for green fluoresncence protein, it was observed that the transfection efficiency at 24 hours post-pulse increased to 17% if the caspase inhibitor was used. Without the caspase inhibitor, very few viable cells and practically no transfected cells are detected, with or without pose-pulse pelleting (FIG. 8b).

Thus, the combination of post-pulse pelleting and the inhibition of apoptosis can improve the electrotransfection efficiency of human CD34+ stem cells and therefore, this method can be applied in therapies demanding transient gene expression. For example, this method can result in a stem cell transfection level that is sufficient for selection of stable clones for long term gene therapy and tissue reconstruction.

Figure 9:
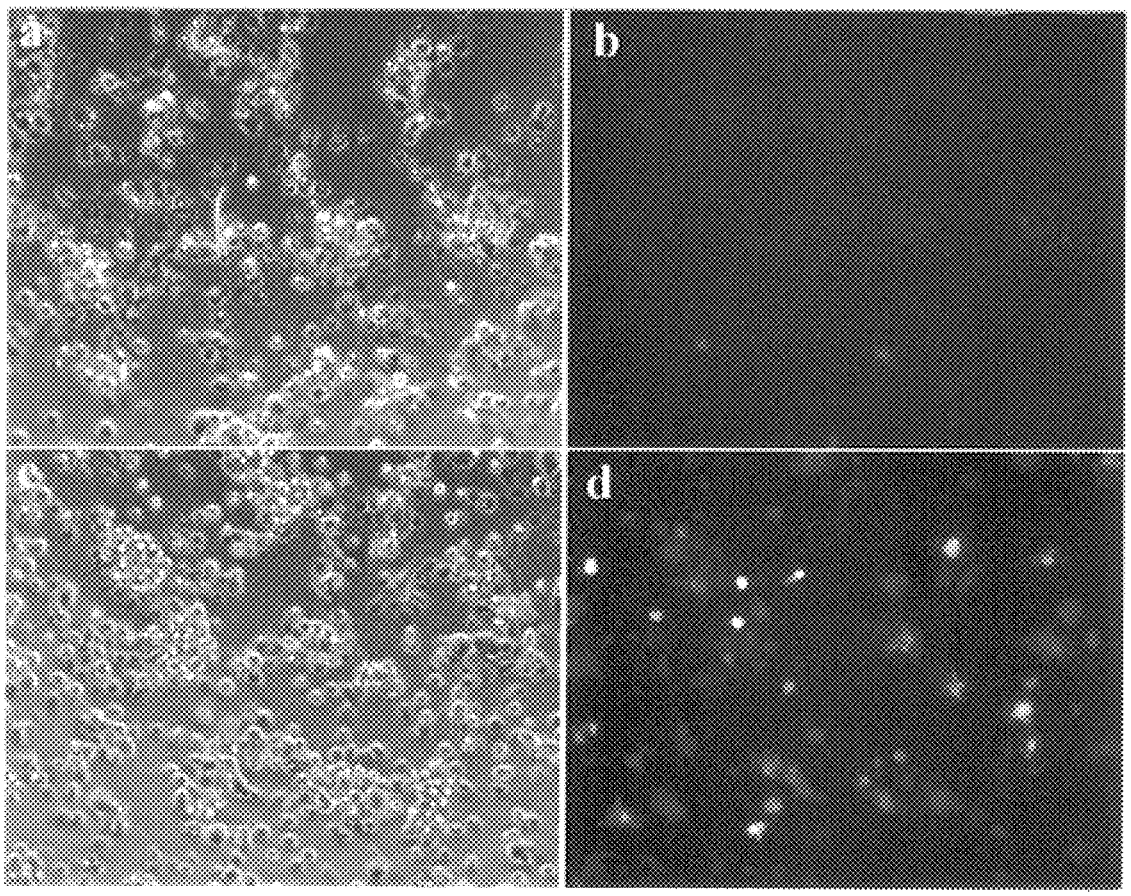
FIGS. 9a–d is a composite of phase contrast (a,c) and fluorescent (b,d) microscopic representations of tranfected mouse bone marrow dendritic BM-DC cells incubated without (a,b) or with (c,d) 120 uM caspase inhibitor.

In another illustration of this embodiment, the transfection efficiency of mouse BM-DC cells, was investigated. Briefly, BM-DC cells were generated by culturing the female Balb/c mice bone marrow stem cells using an improved culture method (Lutz et al., 1999, supra). After 10 days of expansion, the BM-DC cells were elctroporated by four 400 μs, 2 kV/cm pulses, in the presence of 400 μg/ml of pEGFP-N1. Following 20 min of incubation, the BM-DC were transferred to culture medium. Using the plasmids coding for green fluorescence protein, it was observed that the transfection efficiency was limited by apoptosis of electroporated cells. Without caspase inhibitors, the cells expressing green fluorescence protein was about 1–2% at 24 hours after pulsing (FIGS. 9a and 9b). When 120 μM of caspase inhibitor was used in the post-pulse culture medium, the percentage of transfected cells increased to 15–30% (FIGS. 9b and 9d).

TABLE 1

The effect of DNA and caspase inhibitor on the apoptosis and luciferase expression of L1210 subclones and NFS-70 lymphoma

| Cells | No DNA | Apoptosis (%) | | Relative luciferase expression (inhibitor $^1$/inhibitor) (assayed at 24 hour) | | Relative luciferase expression (inhibitor $^1$/inhibitor) (assayed at 48 hour) | |
|---|---|---|---|---|---|---|---|
| | | No inhibitor | 120 μM inhibitor | No inhibitor | 120 μM inhibitor | No inhibitor | 120 μM inhibitor |
| L1210[#] | 2 | <5* | — | — | — | — | — |
| Subclone 3-3[#] | 2 | 59 ± 5[&] | 2 ± 2 | 1 | 4.4 ± 1.3 | 1 | 28 ± 5 |
| Subclone 4[#] | 2 | 38 ± 8[&] | 2 ± 2 | 1 | 4.6 ± 1.3 | — | — |
| Subclone 6[#] | 2 | 53 ± 8[&] | 2 ± 2 | 1 | 8.0 ± 2 | — | — |
| Subclone 7-15.6[@] | 2 | <5* | — | — | — | — | — |
| NFS-70[@] | 0 | 12 ± 5* | 0 | 1 | 4.6 ± 0.4 | 1 | 37 ± 8 |

[#]cells were pulsed in the presence of 600 μg/ml luciferase plasmids.
[@]cells were pulsed in the presence of 160 μg/ml luciferase plasmids.
[&]apoptosis was assayed 6 hours after pulsing.
*apoptosis was assayed 24 hours after pulsing.

TABLE 2

The effect of DNA on the apoptosis of subclone 3–3 of L1210 lymphoma

| E (kV/cm) | No DNA | | Plasmid with Promoter (800 μg/ml) | | Plasmid without Promoter (800 μg/ml) | | Salmon Salmon Sperm DNA (170 μg/ml) |
|---|---|---|---|---|---|---|---|
| | Luciferase expression pg/million cell | Apoptosis (%) | Luceriferase expression pg/million cell | Apoptosis (%) | Luceriferase expression pg/million cell | Apoptosis (%) | Apoptosis (%) |
| 1.67 | 0 | 5 | 130 ± 40 | 82 ± 2 | 0 | 82 ± 1 | 31 ± 14 |
| 2.0 | 0 | 5 | 140 ± 60 | 88 ± 3 | 0 | 91 ± 5 | 42 ± 30 |

TABLE 3

Apoptosis of subclone 3-3 of L1210 induced by DOTAP Vesicle-Induced Transfection

| Lipid/DNA charge ratio | DNA final concentration (μg/ml) | DOTAP final concentration (μg/ml) | Viability (%) | Apoptosis (%) | GFP* expressed cells (%) | Apoptosis among GFP* expressed cells (%) |
|---|---|---|---|---|---|---|
| 0.5 | 60  | 80  | >90 | <5 | <5 | 52 ± 13 |
| 0.5 | 120 | 160 | >90 | <5 | <5 | 47 ± 6  |
| 1   | 60  | 160 | >90 | <5 | <5 | 75 |
| 1   | 120 | 320 | >90 | <5 | <5 | 95 |
| ∞   | 0   | 320 | >90 | <5 | 0  | 0  |

*GFP-green fluorescence protein

From the foregoing, it will be obvious to those skilled in the art that various modifications in the above-described methods, and compositions can be made without departing from the spirit and scope of the invention. Accordingly, the invention may be embodied in other specific forms without departing from the spirit of essential characteristics thereof. Present embodiments and examples, therefore, are to be considered in all respects as illustrative and not restrictive, and all changes which come within the meaning and range of equivalency of the claims are therefore intended to be embraced therein.

What is claimed is:

1. A method of increasing the efficiency of transfection of cells by inhibiting apoptosis induced by DNA uptake comprising the step of exposing the cells to an inhibitor of apoptosis in an amount sufficient to increase the transfection efficiency over cells transfected in the absence of the apoptosis inhibitor.

2. The method of claim 1, wherein the inhibitor of apoptosis is a caspase inhibitor.

3. The method of claim 2, wherein the caspase inhibitor is selected from the group consisting of fluoromethyl ketone, and a derivative thereof.

4. The method of claim 3, wherein the concentration of caspase inhibitor is between about 1 $\mu$M to about 1 mM.

5. The method of claim 1, wherein the inhibitor of apoptosis is a calpain inhibitor.

6. The method of claim 1, wherein the cells are lymphoma cells.

7. The method of claim 1, wherein the cells are transfected by electroporation.

8. The method of claim 1, wherein the cells are exposed to the apoptosis inhibitor during transfection.

9. The method of claim 1, wherein the cells are exposed to the apoptosis inhibitor after transfection.

* * * * *